(12) United States Patent
Moffitt et al.

(10) Patent No.: US 10,004,902 B2
(45) Date of Patent: *Jun. 26, 2018

(54) DEVICES AND METHODS USING A PATHOLOGICAL FREQUENCY IN ELECTRICAL STIMULATION FOR PAIN MANAGEMENT

(71) Applicant: Boston Scientific Neuromodulation Corporation, Valencia, CA (US)

(72) Inventors: Michael A. Moffitt, Valencia, CA (US); Stephen Carcieri, Los Angeles, CA (US); Hemant Bokil, Cambridge, MA (US); Rafael Carbunaru, Valley Village, CA (US)

(73) Assignee: Lowe Graham Jones PLLC, Valencia, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/799,234

(22) Filed: Oct. 31, 2017

(65) Prior Publication Data
US 2018/0050205 A1    Feb. 22, 2018

Related U.S. Application Data

(63) Continuation of application No. 14/861,605, filed on Sep. 22, 2015, now Pat. No. 9,833,622.
(Continued)

(51) Int. Cl.
| A61N 1/00 | (2006.01) |
| A61N 1/36 | (2006.01) |
| A61B 5/0484 | (2006.01) |

(52) U.S. Cl.
CPC ..... A61N 1/36071 (2013.01); A61N 1/36135 (2013.01); A61N 1/36139 (2013.01);
(Continued)

(58) Field of Classification Search
CPC ................ A61N 1/36071; A61N 1/36135
(Continued)

(56) References Cited

U.S. PATENT DOCUMENTS

| 4,813,418 A | 3/1989 | Harris |
| 6,067,474 A | 5/2000 | Schulman et al. |

(Continued)

FOREIGN PATENT DOCUMENTS

| DE | 10318071 A1 | 11/2004 |
| WO | 02/09808 A1 | 2/2002 |
| WO | 2009/055127 A1 | 4/2009 |

OTHER PUBLICATIONS

Larson, J. et al., "Reversal of LTP by theta frequency stimulation", Brain Research, Elsevier, Amsterdam NL, vol. 600 No. 1, Jan. 8, 1993, pp. 97-102.
(Continued)

*Primary Examiner* — Nadia A Mahmood
(74) *Attorney, Agent, or Firm* — Lowe Graham Jones PLLC; Bruce E. Black

(57) ABSTRACT

An electrical stimulation system includes an implantable control module configured and arranged for implantation in a body of a patient. The implantable control module includes a processor that generates and delivers electrical stimulation pulses or pulse bursts at a pathological frequency or with a temporal separation between pulses or pulse bursts individually selected based on a pre-determined distribution function based on a pre-selected pathological frequency.

20 Claims, 10 Drawing Sheets

Related U.S. Application Data

(60) Provisional application No. 62/053,414, filed on Sep. 22, 2014.

(52) U.S. Cl.
CPC ..... *A61N 1/36171* (2013.01); *A61N 1/36178* (2013.01); *A61B 5/0484* (2013.01); *A61N 1/36185* (2013.01)

(58) Field of Classification Search
USPC ................................................ 607/2, 45, 46
See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |
| 7,450,997 B1 | 11/2008 | Pianca et al. |
| 7,672,734 B2 | 3/2010 | Anderson et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,917,221 B2 | 3/2011 | Tass |
| 7,949,395 B2 | 5/2011 | Kuzma |
| 7,974,698 B2 | 7/2011 | Tass et al. |
| 7,974,706 B2 | 7/2011 | Moffitt et al. |
| 8,000,794 B2 | 8/2011 | Lozano |
| 8,000,795 B2 | 8/2011 | Lozano |
| 8,000,796 B2 | 8/2011 | Tass et al. |
| 8,078,275 B2 | 12/2011 | Lozano |
| 8,116,874 B2 | 2/2012 | Tass |
| 8,175,710 B2 | 5/2012 | He |
| 8,224,450 B2 | 7/2012 | Brase |
| 8,271,094 B1 | 9/2012 | Moffitt et al. |
| 8,280,514 B2 | 10/2012 | Lozano et al. |
| 8,295,944 B2 | 10/2012 | Howard et al. |
| 8,346,365 B2 | 1/2013 | Lozano |
| 8,364,278 B2 | 1/2013 | Pianca et al. |
| 8,380,304 B2 | 2/2013 | Lozano |
| 8,391,985 B2 | 3/2013 | McDonald |
| 8,463,378 B2 | 6/2013 | Tass |
| 8,463,386 B2 | 6/2013 | Tass |
| 8,538,547 B2 | 9/2013 | Tass et al. |
| 8,565,883 B2 | 10/2013 | Lozano |
| 8,612,006 B2 | 12/2013 | Lozano et al. |
| 8,868,191 B2 | 10/2014 | Lozano |
| 9,227,066 B2 | 1/2016 | Lozano |
| 2003/0191506 A1 | 10/2003 | Shloznikov |
| 2004/0210271 A1 | 10/2004 | Campen et al. |
| 2005/0075696 A1 | 4/2005 | Forsberg et al. |
| 2005/0216071 A1 | 9/2005 | Devlin et al. |
| 2006/0015153 A1 | 1/2006 | Bradford et al. |
| 2006/0212090 A1 | 9/2006 | Lozano et al. |
| 2007/0142874 A1* | 6/2007 | John .................. A61N 1/3605 607/45 |
| 2007/0150036 A1 | 6/2007 | Anderson |
| 2007/0225674 A1 | 9/2007 | Molnar et al. |
| 2008/0071325 A1 | 3/2008 | Bradley |
| 2008/0215113 A1 | 9/2008 | Pawlowicz |
| 2009/0082829 A1 | 3/2009 | Panken et al. |
| 2009/0112281 A1 | 4/2009 | Miyazawa et al. |
| 2009/0187222 A1 | 7/2009 | Barker |
| 2009/0276021 A1 | 11/2009 | Meadows et al. |
| 2010/0268298 A1 | 3/2010 | Pianca et al. |
| 2010/0076535 A1 | 5/2010 | Pianca et al. |
| 2011/0004267 A1 | 1/2011 | Meadows et al. |
| 2011/0077720 A1 | 3/2011 | Torgerson et al. |
| 2011/0078900 A1 | 4/2011 | Pianca et al. |
| 2011/0130817 A1 | 6/2011 | Chen |
| 2011/0130818 A1 | 6/2011 | Chen |
| 2011/0201977 A1 | 8/2011 | Tass |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0274273 A1 | 11/2012 | Jacobs et al. |
| 2012/0316615 A1 | 12/2012 | DiGiore et al. |
| 2013/0105071 A1 | 5/2013 | DiGiore et al. |
| 2013/0218239 A1 | 8/2013 | Grill et al. |
| 2013/0231713 A1 | 9/2013 | De Ridder |
| 2013/0289385 A1 | 10/2013 | Lozano et al. |
| 2013/0317583 A1 | 11/2013 | Pianca |
| 2013/0317585 A1 | 11/2013 | Barker |
| 2013/0317586 A1 | 11/2013 | Pianca |
| 2013/0317587 A1 | 11/2013 | Barker |
| 2013/0317588 A1 | 11/2013 | Howard et al. |
| 2014/0025133 A1 | 1/2014 | Lozano |
| 2014/0081349 A1 | 3/2014 | Lee et al. |
| 2014/0277281 A1 | 9/2014 | Grandhe |
| 2016/0030666 A1 | 2/2016 | Lozano et al. |

OTHER PUBLICATIONS

International Search Report and Written Opinion for Application PCT/US2015/051478 dated Dec. 9, 2015, 12 pages.

Official Communication for U.S. Appl. No. 14/861,605 dated Feb. 3, 2017.

Official Communication for U.S. Appl. No. 14/861,605 dated Jul. 28, 2017.

* cited by examiner

DEVICES AND METHODS USING A PATHOLOGICAL FREQUENCY IN ELECTRICAL STIMULATION FOR PAIN MANAGEMENT

CROSS-REFERENCE TO RELATED APPLICATIONS

This application is a continuation of U.S. patent application Ser. No. 14/861,605, filed Sep. 22, 2015, which claims the benefit under 35 U.S.C. § 119(e) of U.S. Provisional Patent Application Ser. No. 62/053,414, filed Sep. 22, 2014, both of which are incorporated herein by reference.

FIELD

The present invention is directed to the area of implantable electrical stimulation systems and methods of making and using the systems. The present invention is also directed to implantable electrical stimulation systems that use a pathological frequency to stimulate for pain management, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a non-transitory computer-readable medium having processor-executable instructions for delivering an electrical stimulation signal, the processor-executable instructions when installed onto a device enable the device to perform actions, including: generating an electrical stimulation signal at a pathological frequency in a range of 4 to 8 Hz; and delivering the electrical stimulation signal to one or more selected electrodes of an attached lead.

In at least some embodiments, the electrical stimulation signal includes a series of pulses at the pathological frequency. In at least some embodiments, the electrical stimulation signal includes a series of bursts at the pathological frequency, where each burst comprises a plurality of pulses within the burst and at a frequency of at least 500 Hz. In at least some embodiments, the electrical stimulation signal includes a base stimulation signal at the pathological frequency and a series of bursts at the pathological frequency, where each burst includes a plurality of pulses within the burst and at a frequency of at least 500 Hz.

In at least some embodiments, the actions further include sensing a biosignal. In at least some embodiments, the actions further include repeating the generating, delivering, and sensing actions based on an analysis of the biosignal.

Another embodiment is a non-transitory computer-readable medium having processor-executable instructions for delivering an electrical stimulation signal, the processor-executable instructions when installed onto a device enable the device to perform actions, including: generating electrical stimulation pulses or pulse bursts with a temporal separation between pulses or pulse bursts individually selected based on a pre-determined distribution function based on a pre-selected pathological frequency; and delivering the electrical stimulation pulses or pulse bursts to one or more selected electrodes of an attached lead.

In at least some embodiments, the pre-determined distribution function is a periodic repeating distribution function. In at least some embodiments, the pre-determined distribution function is a sine distribution. In at least some embodiments, the pre-determined distribution function is a normal distribution. In at least some embodiments, the pre-determined distribution function is a distribution function that resets with each pulse or burst of pulses.

In at least some embodiments, the actions further include sensing a biosignal. In at least some embodiments, the actions further include repeating the generating, delivering, and sensing actions based on an analysis of the biosignal.

Yet another embodiment is an electrical stimulation system that includes an implantable control module configured and arranged for implantation in a body of a patient. The control module is configured and arranged to provide electrical stimulation signals to an electrical stimulation lead coupled to the implantable control module for stimulation of patient tissue. The implantable control module includes an antenna configured and arranged to receive input, and a processor in communication with the antenna and configured and arranged to perform the following actions: generating electrical stimulation pulses or pulse bursts with a temporal separation between pulses or pulse bursts individually selected based on a pre-determined distribution function based on a pre-selected pathological frequency; and delivering the electrical stimulation pulses or pulse bursts to one or more selected electrodes of an attached lead.

In at least some embodiments, the pre-determined distribution function is a periodic repeating distribution function. In at least some embodiments, the pre-determined distribution function is a sine distribution. In at least some embodiments, the pre-determined distribution function is a normal distribution. In at least some embodiments, the pre-determined distribution function is a distribution function that resets with each pulse or burst of pulses.

In at least some embodiments, the system further includes a sensor in communication with the control module, wherein the actions further include sensing a biosignal using the sensor. In at least some embodiments, the system further includes an electrical stimulation lead coupleable to the implantable control module and including a plurality of electrodes disposed along a distal end portion of the electrical stimulation lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems that use a pathological frequency to stimulate for pain management, as well as methods of making and using the leads and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference. It will also be understood that other electrical stimulation systems can be used including a system that has an implantable lead coupled to an external control module (such as an external trial stimulator).

Figure 1:
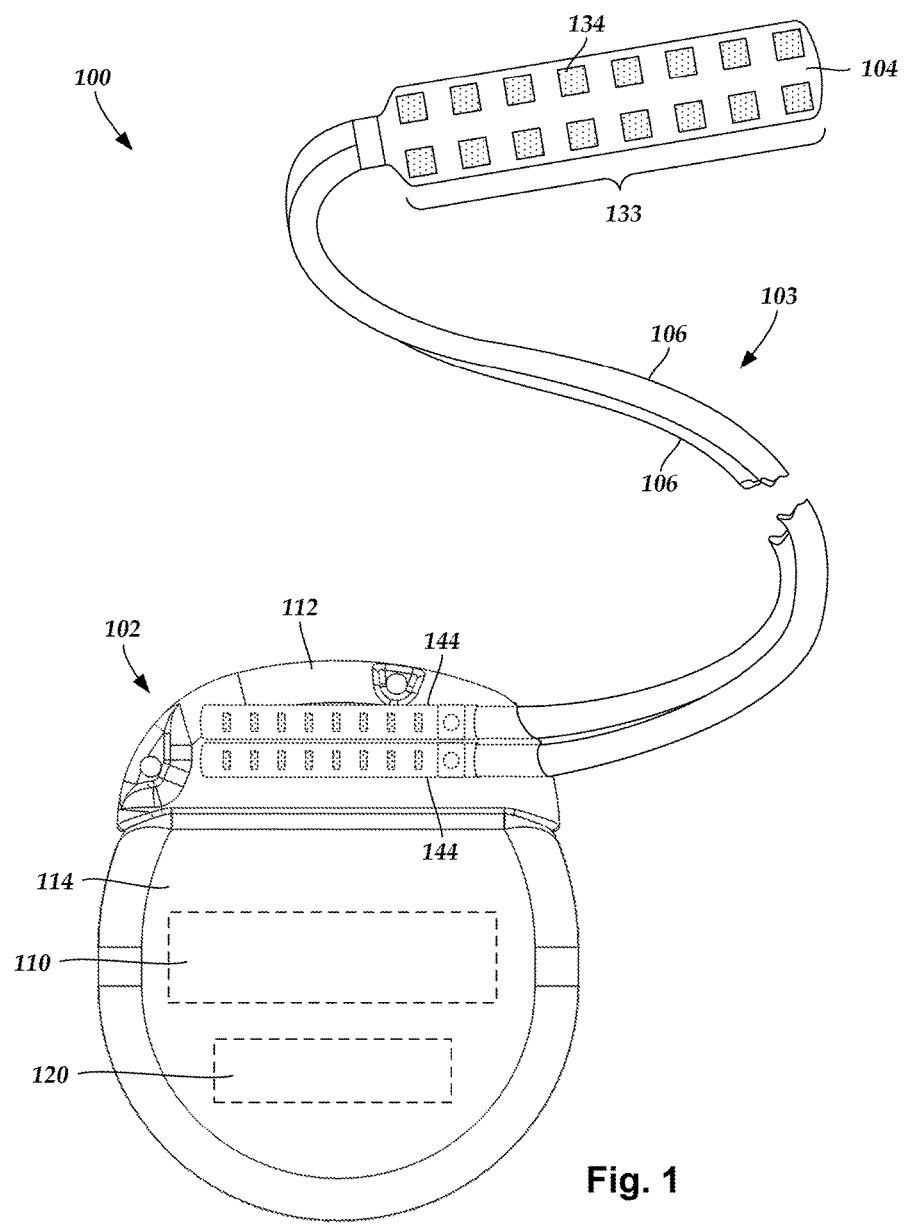
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (e.g., 310 in FIG. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
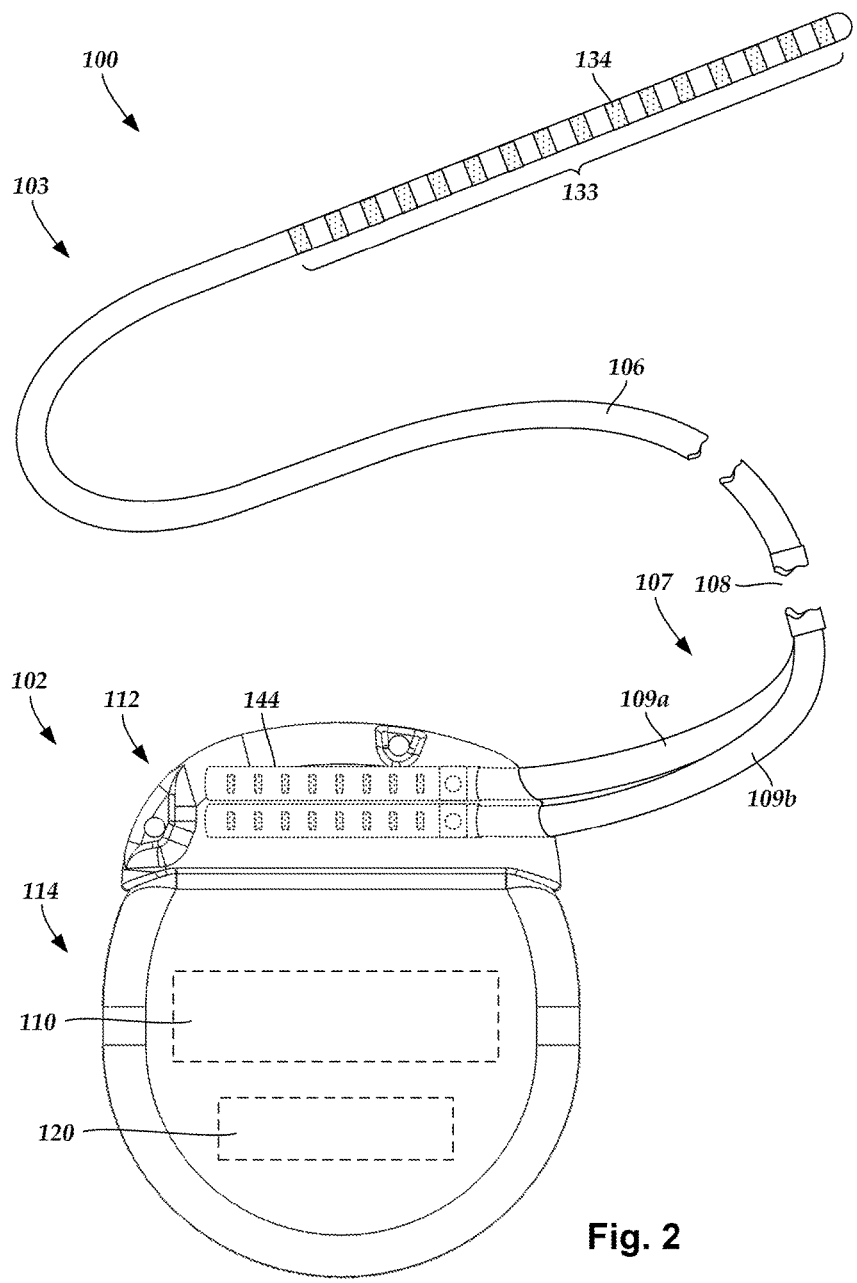
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
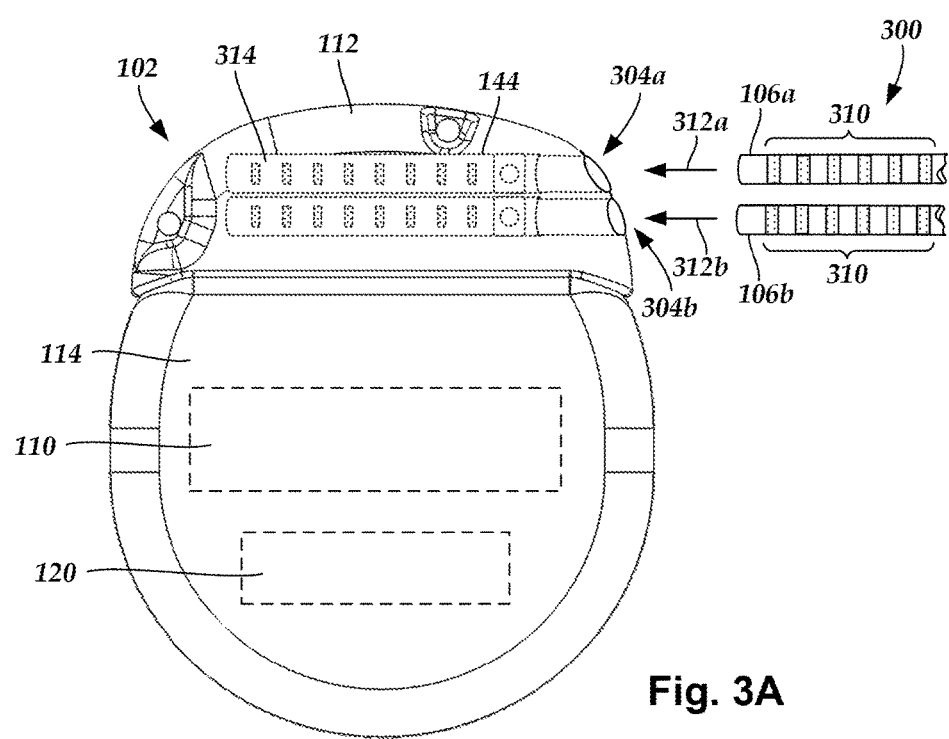
FIG. 3A is a schematic view of one embodiment of the control module of FIG. 1 configured and arranged to electrically couple to an elongated device, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIG. 3A). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
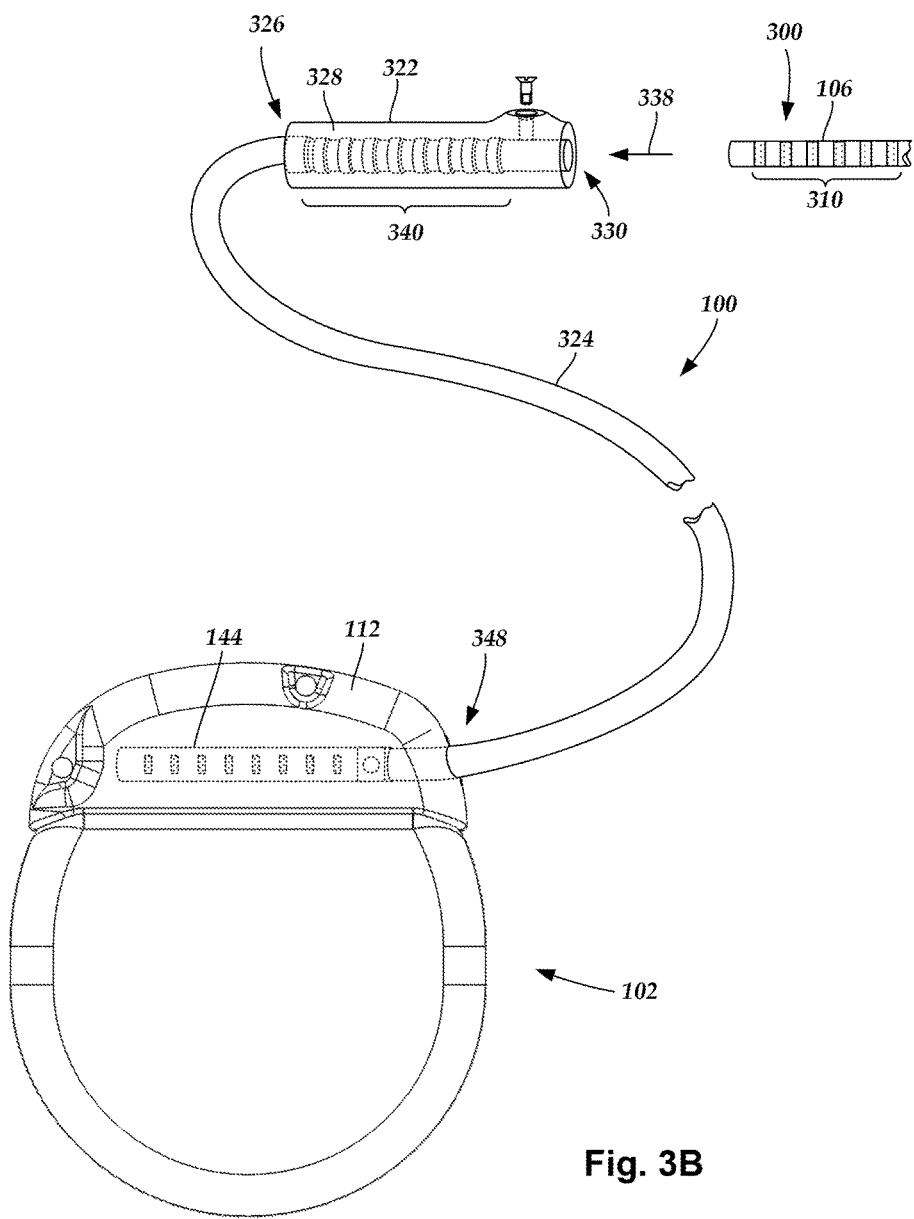
FIG. 3B is a schematic view of one embodiment of a lead extension configured and arranged to electrically couple the elongated device of FIG. 2 to the control module of FIG. 1, according to the invention.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Figure 4:
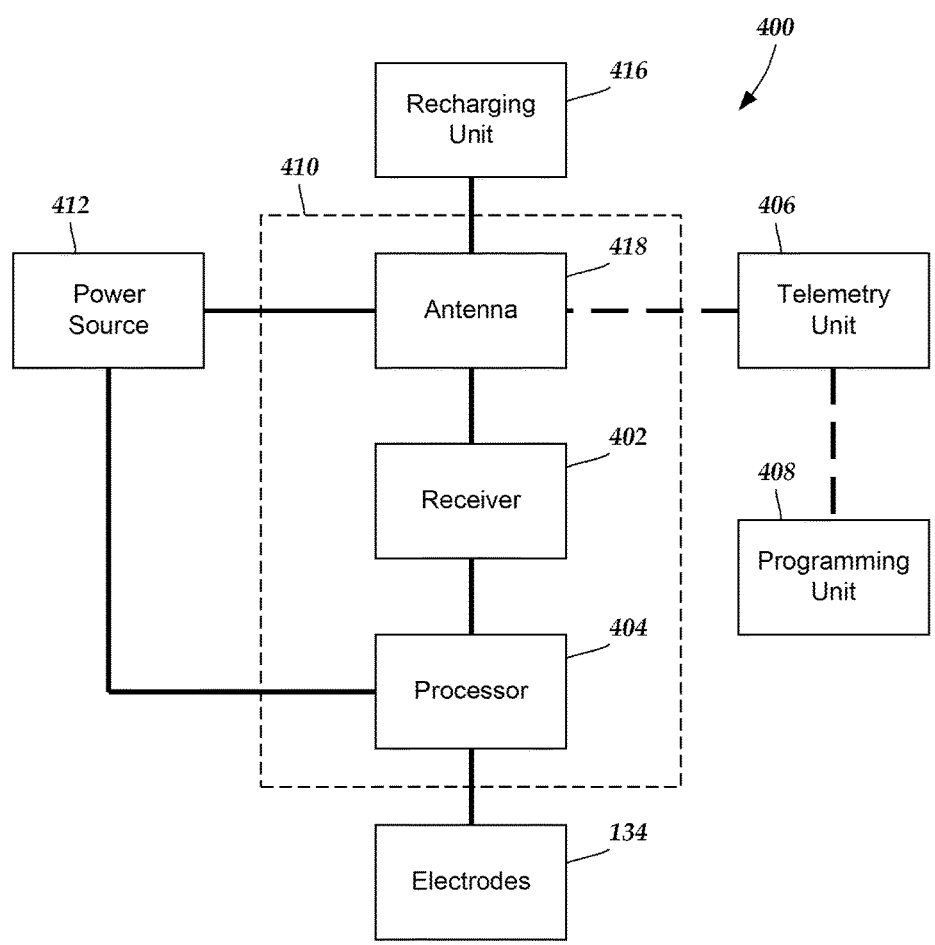
FIG. 4 is a schematic block diagram of one embodiment of an electrical stimulation system, according to the invention.

FIG. 4 is a schematic overview of one embodiment of components of an electrical stimulation system 400 including an electronic subassembly 410 disposed within a control module. It will be understood that the electrical stimulation system can include more, fewer, or different components and can have a variety of different configurations including those configurations disclosed in the stimulator references cited herein.

Some of the components (for example, a power source 412, an antenna 418, a receiver 402, and a processor 404) of the electrical stimulation system can be positioned on one or more circuit boards or similar carriers within a sealed housing of an implantable pulse generator, if desired. Any power source 412 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 418 or a secondary antenna. The external power source can be in a device that is mounted on the skin of the user or in a unit that is provided near the user on a permanent or periodic basis.

If the power source 412 is a rechargeable battery, the battery may be recharged using the optional antenna 418, if desired. Power can be provided to the battery for recharging by inductively coupling the battery through the antenna to a recharging unit 416 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 404 is generally included to control the timing and electrical characteristics of the electrical stimulation system. For example, the processor 404 can, if desired, control one or more of the timing, frequency, strength, duration, and waveform of the pulses. In addition, the processor 404 can select which electrodes can be used to provide stimulation, if desired. In some embodiments, the processor 404 selects which electrode(s) are cathodes and which electrode(s) are anodes. In some embodiments, the processor 404 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 408 that, for example, allows modification of pulse characteristics. In the illustrated embodiment, the processor 404 is coupled to a receiver 402 which, in turn, is coupled to the optional antenna 418. This allows the processor 404 to receive instructions from an external source to, for example, direct the pulse characteristics and the selection of electrodes, if desired.

In one embodiment, the antenna 418 is capable of receiving signals (e.g., RF signals) from an external telemetry unit 406 which is programmed by the programming unit 408. The programming unit 408 can be external to, or part of, the telemetry unit 406. The telemetry unit 406 can be a device that is worn on the skin of the user or can be carried by the user and can have a form similar to a pager, cellular phone, or remote control, if desired. As another alternative, the telemetry unit 406 may not be worn or carried by the user but may only be available at a home station or at a clinician's office. The programming unit 408 can be any unit that can provide information to the telemetry unit 406 for transmission to the electrical stimulation system 400. The programming unit 408 can be part of the telemetry unit 406 or can provide signals or information to the telemetry unit 406 via a wireless or wired connection. One example of a suitable programming unit is a computer operated by the user or clinician to send signals to the telemetry unit 406.

The signals sent to the processor 404 via the antenna 418 and the receiver 402 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 400 to cease operation, to start operation, to start charging the battery, or to stop charging the battery. In other embodiments, the stimulation system does not include the antenna 418 or receiver 402 and the processor 404 operates as programmed.

Optionally, the electrical stimulation system 400 may include a transmitter (not shown) coupled to the processor 404 and the antenna 418 for transmitting signals back to the telemetry unit 406 or another unit capable of receiving the signals. For example, the electrical stimulation system 400 may transmit signals indicating whether the electrical stimulation system 400 is operating properly or not or indicating when the battery needs to be charged or the level of charge remaining in the battery. The processor 404 may also be capable of transmitting information about the pulse characteristics so that a user or clinician can determine or verify the characteristics.

Methods of communication between devices or components of a system can include wired or wireless (e.g., RF, optical, infrared, near field communication (NFC), Bluetooth™, or the like) communications methods or any combination thereof. By way of further example, communication methods can be performed using any type of communication media or any combination of communication media including, but not limited to, wired media such as twisted pair, coaxial cable, fiber optics, wave guides, and other wired media and wireless media such as acoustic, RF, optical, infrared, NFC, Bluetooth™ and other wireless media. These communication media can be used for communications arrangements in the external programming unit 406 or as antenna 412 or as an alternative or supplement to antenna 412.

It is known that brain waves and other waves can adopt oscillatory patterns within a number of different frequency bands. For example, brain wave bands have been detected using EEG and other methods and have been designated as, for example, delta, theta, alpha, beta, and gamma bands and the like. It at least some instances particular frequencies or frequency ranges or correlations between them within these bands can be indicative of abnormal conditions. As an example, it has been found that pain signals can be associated with frequencies in the theta band (approximately 4-8 Hz) that are shifted in frequency (for example, elevated) from a normal, "pain-free" frequency or frequency range within that band.

Although not wishing to be bound by any particular theory, it is thought that stimulating neural tissue at or near these characteristic frequencies or at or near a normal or "pain-free" frequency or frequency range can facilitate treatment of pain and, perhaps, shift neuronal activity to the desired frequency or frequency range or pattern. As an example, stimulating neural tissue in the spinal cord or elsewhere may alleviate or reduce pain. In at least some embodiments, a frequency in the theta band (4-8 Hz) is selected as a desired pathological frequency and neural tissue is stimulated at or near this pathological frequency as described in the various embodiments below. Although stimulation using a frequency in the theta band is described in the embodiments below, it will be understood that other frequencies, including those in bands other than the theta band such as the delta, alpha, beta, or gamma bands or at higher or lower frequencies (for example, in the range of 1 to 1000 Hz), can also be used for stimulation. In at least some embodiments, stimulating at the selected pathological frequency can disrupt or desynchronize undesirable synchronized neural signals at another frequency, such as another frequency in the theta band.

The desired stimulation frequency can be selected based on pathological information. In at least some embodiments, the desired stimulation frequency can be determined by measurements of biosignals from the patient. For example, an electroencephalograph (EEG) of the patient can be used to determine a desired stimulation frequency. The EEG may also be used to indicate pathological frequencies or frequency ranges from the biosignals that are indicative of pain or other conditions. In other embodiments, a desired stimulation frequency can be based on aggregated data from a population of patients. This population may be a general population or may be selected based on one or more factors such as, but not limited to, age, gender, race, height, weight, physical conditioning, existence of a particular medical condition or symptom, or the like. In yet other embodiments, the desired stimulation frequency may be selected based on stimulation trials conducted with the patient. In further embodiments, any combination of biosignal measurements, population data, or stimulation trials may be used to aid in selecting a stimulation frequency.

Electrical stimulation can be performed at a variety of different sites within the patient. For example, the stimulation may be applied at the site of the pain or other condition or within the brain. In at least some embodiments, electrical stimulation is applied to the spinal cord. Examples of spinal cord stimulation systems are described above in the references cited above. Stimulation may be performed to any portion of the spinal cord including the dorsal columns, dorsal horns, dorsal roots, or any combination thereof. Examples of dorsal root stimulation can be found at, for example, U.S. Patent Applications Publication Nos. 2013/0317583; 2013/0317585; 2013/0317586; 2013/0317587; and 2013/0317588, all of which are incorporated by reference. Examples of dorsal horn stimulation can be found at, for example, U.S. Patent Application Publication No. 2014/0081349, incorporated herein by reference. In at least some embodiments, electrical stimulation may be performed at a portion of the spinal cord at or above the region in which nerves from the body parts experiencing pain or another condition for treatment connect to the spinal cord. In at last some embodiments, the electrical stimulation is applied to provide a parathesia or tingling feeling within the body part to be treated. In at least some embodiments, the electrical stimulation may produce a sub-parathesia effect that also provides treatment for pain or other conditions.

The electrical stimulation is produced with at least one electrode acting as an anode and at least one electrode acting as a cathode. Any electrode(s) used to provide the electrical stimulation can be located on a lead or microstimulator. In at least some embodiments, an electrode on the control module can act as an anode or cathode. In the embodiments described below, the electrical stimulation is characterized as pulses of relatively steady amplitude current. It will be recognized, however, that other pulse shapes (for example, pulses that ramp up, ramp down, or both or pulses with steady or varying voltage) can also be used for electrical stimulation.

Figure 5A:
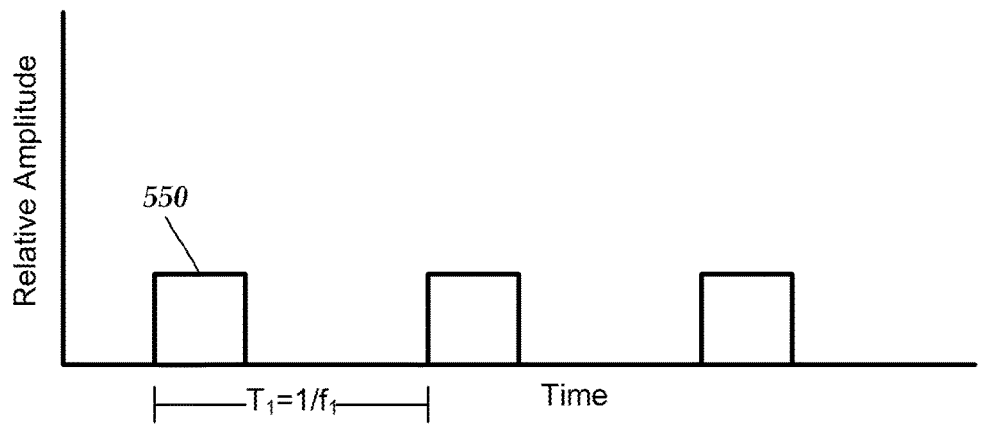
FIG. 5A is a graph of one embodiment of stimulation signals in the form of pulses generated and delivered over time, according to the invention.

FIG. 5A is a graph illustrating one embodiment of a stimulation scheme. In this embodiment, the control module generates pulses 550 at a frequency $f_1$ that corresponds to a pathological frequency selected as described above. The period $T_1$ between pulses 550 is $1/f_1$. For example, the pathological frequency can be in the theta band of 4 to 8 Hz. It has also been found that peripheral stimulation of pain receptors (nociceptive stimulation) causes increased coherence between the theta band and the gamma band (25 to 90 Hz). Accordingly, stimulation at a pathological frequency in the gamma band (25 to 90 Hz) can be effective.

Figure 5B:
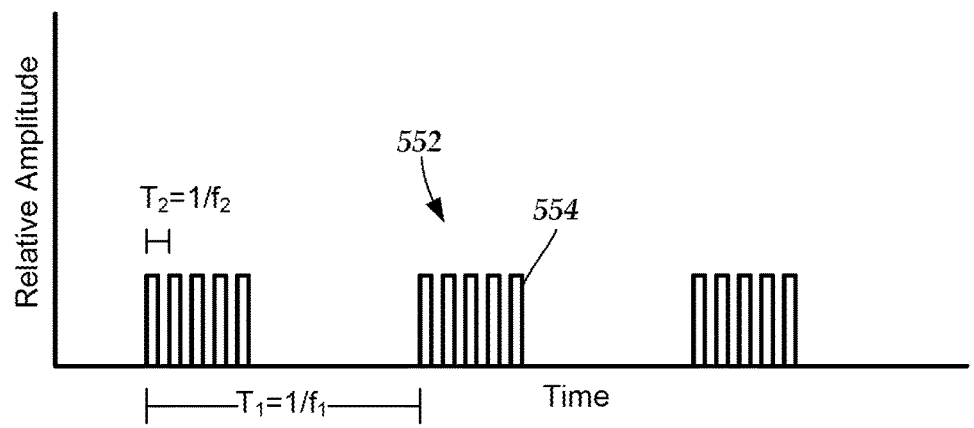
FIG. 5B is a graph of one embodiment of stimulation signals in the form of bursts of pulses generated and delivered over time, according to the invention.

FIG. 5B is a graph illustrating another embodiment of a stimulation scheme in which the control module generates a burst 552 of pulses 554. The bursts occur at a regular frequency $f_1$ that corresponds to a selected pathological frequency. For example, the pathological frequency can be in the theta band of 4 to 8 Hz. The period $T_1$ between pulses 550 is $1/f_1$. The pulses 554 within a burst 552 occur at a higher frequency $f_2$. In at least some embodiments, the pulses occur at a frequency $f_2$ (with a period $T_2=1/f_2$) that is in the range of 500 Hz to 5 kHz. The burst 552 can include any number of pulses 554. In at least some embodiments, a burst includes 2 to 100 pulses or 2 to 20 pulses or 2 to 10 pulses.

Figure 6A:
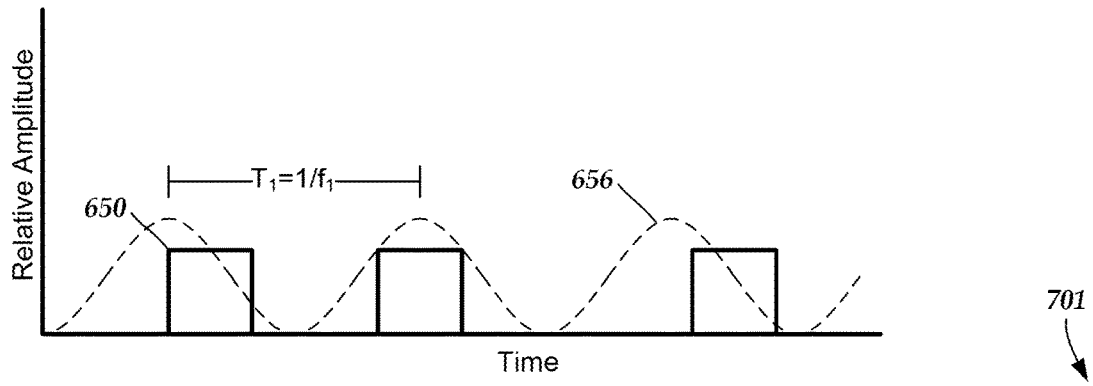
FIG. 6A is a graph of one embodiment of stimulation signals in the form of pulses generated and delivered over time based on a periodic repeating distribution function, according to the invention.
Figure 6B:
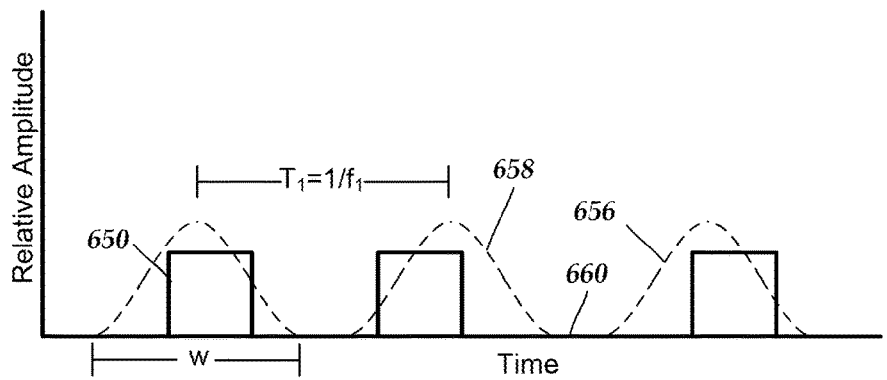
FIG. 6B is a graph of one embodiment of stimulation signals in the form of pulses generated and delivered over time based on a compound periodic repeating distribution function, according to the invention.

Although not wishing to be bound by any particular theory, it may be beneficial to provide electrical stimulation that is not presented strictly at a regular frequency, but where there is some variation in the temporal separation between the pulses or bursts. This is similar to the body's natural rhythms which are often variable in period and frequency. Accordingly, a desired stimulation frequency can be selected which represents the average period between pulses and bursts, but the actually delivery of pulses or bursts can be modulated around this center stimulation frequency. FIGS. 6A-7 illustrate embodiments in which the temporal separation between pulses or bursts is variable and determined based on a distribution function that can be disposed about a center stimulation frequency or period.

In at least some embodiments, the distribution function that is used to determine the temporal separation between pulses or bursts is a periodic repeating distribution function. FIG. 6A is a graph illustrating one embodiment of a stimulation scheme in which the control module generates pulses 650 where the period T between pulses is variable and is selected using a periodic repeating distribution function 656 that has a center stimulation frequency $f_1$ (and corresponding center period $T_1=1/f_1$) that can be selected to be a pathological frequency (for example, a theta band frequency in the range of 4-8 Hz.) The distribution function 656 can be normalized for each period and indicates the relative likelihood that a given pulse will begin at that time. In the embodiment illustrated in FIG. 6A, the periodic repeating distribution function is a sine wave with a period of $T_1$. It will be understood that other distribution functions can be used include, but are not limited to, a normal distribution, a square wave function, a triangular function, a gamma distribution function, and the like. Other examples, such as the embodiment illustrated in FIG. 6B, can include a periodic repeating combination distribution function 656 with a distribution section 658 such as a sine wave, normal distribution, square wave, or the like separated by a flat (for example, zero) distribution section 660. Any other suitable combination of functions can also be used. Although the repeating function described herein is periodic, in other embodiments, the repeating function may be repeated in an aperiodic manner with variation in the separation between the repeating functions. Accordingly, any discussion herein regarding the periodic repeating function is also applicable to an aperiodic repeating function.

In at least some of these instances, there can be one or more distribution variables that may be selectable by a clinician, a patient, or both to define a shape of the distribution. As an example, the standard deviation of a normal distribution can be a selectable variable or the width of the sine wave 658 and width of the flat distribution section 660 in the embodiment of FIG. 6B can be selectable variables. The width of a square wave distribution or the width of a triangular distribution (at its base or at half maximum or any other position along the triangle) can also be selectable variables.

Figure 6C:
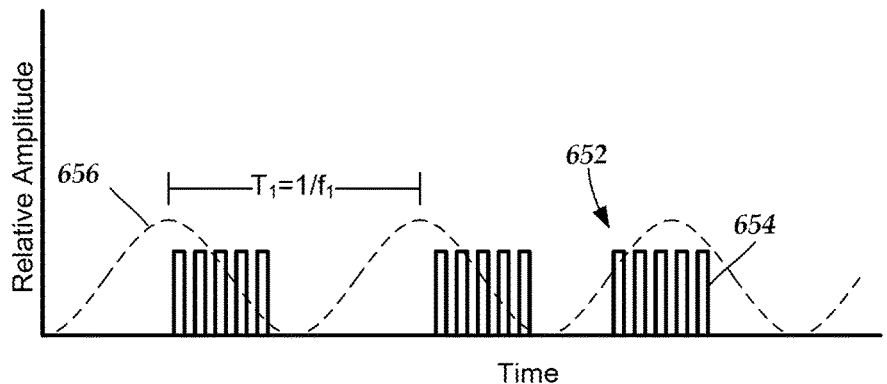
FIG. 6C is a graph of one embodiment of stimulation signals in the form of bursts of pulses generated and delivered over time based on a periodic repeating distribution function, according to the invention.
Figure 7:
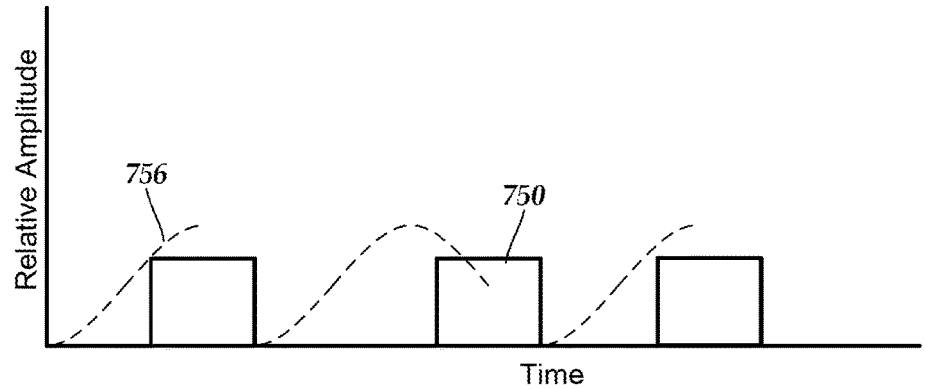
FIG. 7 is a graph of one embodiment of stimulation signals in the form of pulses generated and delivered over time based on a distribution function that is reset with each pulse, according to the invention.

FIG. 6C is a graph illustrating another embodiment of a stimulation scheme in which the control module generates a burst 652 of pulses 654 where the period T between bursts is variable and is selected using a periodic repeating distribution function 656 that has a center frequency $f_1$ (and corresponding center period $T_1=1/f_1$) that can be selected to be a pathological frequency (for example, a theta band frequency in the range of 4-8 Hz.) The distribution function 656 can be normalized and is a function of the relative likelihood that a given pulse will begin at that time. In the embodiment illustrated in FIG. 6C, the periodic repeating distribution function is a sine wave. It will be understood that any of the other distribution functions described with respect to the embodiments of FIGS. 6A and 6B can also be utilized with a burst 652 of pulses 654. The pulses 654 within a burst 652 occur at a higher frequency $f_2$. For example, the pulses may occur at a frequency $f_2$ (with a period $T_2=1/f_2$) that is in the range of 500 Hz to 5 kHz. The burst 652 can include any number of pulses 654. In at least some embodiments, a burst includes 2 to 100 pulses or 2 to 20 pulses or 2 to 10 pulses.

In at least some embodiments, the probability of the next pulse or burst can depend on the previous pulse(s) or burst(s). FIG. 7 illustrates one embodiment in which the likelihood of a pulse 750 occurring at a given time depends on a distribution function 756 (which is partially illustrated for each pulse in FIG. 7). In these embodiments, the distribution function is reset by a triggering occurrence. In the embodiment of FIG. 7, the triggering occurrence can be the end of the preceding pulse (or even the beginning of the preceding pulse with the distribution function being zero during the preceding pulse).

Figure 8A:
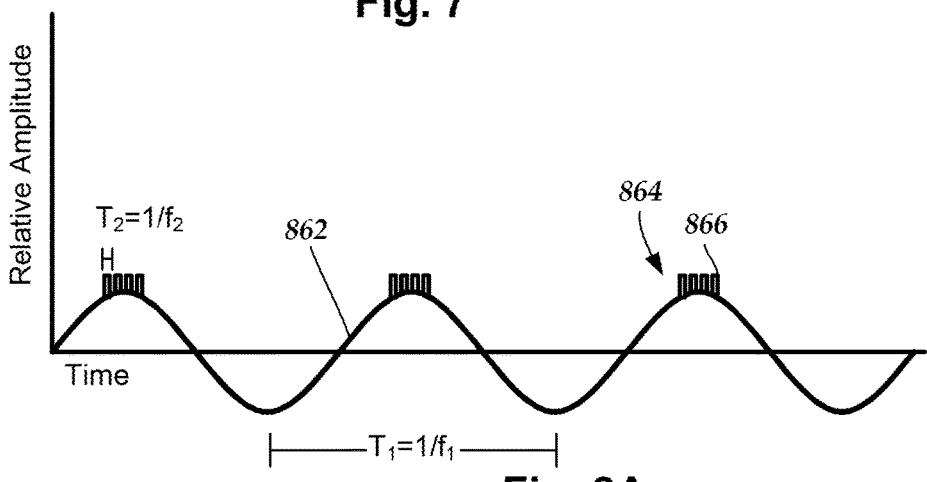
FIG. 8A is a graph of one embodiment of stimulation signals in the form of continuous portion with pulses generated and delivered over time, according to the invention.
Figure 8B:
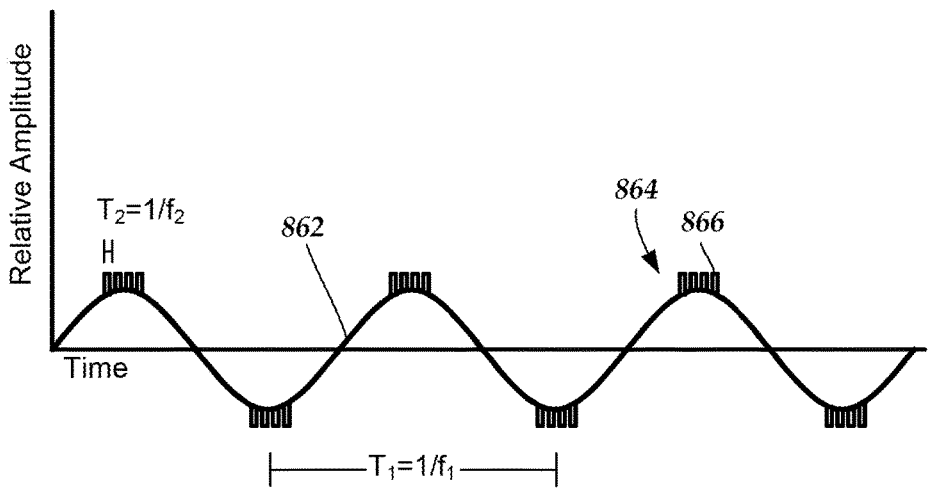
FIG. 8B is a graph of another embodiment of stimulation signals in the form of continuous portion with pulses generated and delivered over time, according to the invention.

FIGS. 8A and 8B illustrate embodiments in which continuous stimulation 862 is produced at a frequency $f_1$ (with a corresponding period $T_1$) with bursts 864 of pulses 866 during every period (FIG. 8A) or half period (FIG. 8B). For example, the pathological frequency can be in the theta band of 4 to 8 Hz. The period $T_1$ is $1/f_1$. The pulses 866 within a burst 864 occur at a higher frequency $f_2$. In at least some embodiments, the pulses occur at a frequency $f_2$ (with a period $T_2=1/f_2$) that is in the range of 500 Hz to 5 kHz.

In at least some embodiments, the electrical stimulation signal (such as the signals illustrated in FIGS. 5A-8B) can be provided on a continuous basis or at regular or irregular intervals which may be programmed into the control module. In at least some embodiments, the patient may direct the initiation of electrical stimulation using an external device that is in communication with the control module.

In at least some embodiments, the system may include one or more sensors or be in communication with one or more sensors that monitor one or more biosignals. Examples of suitable biosignals include, but are not limited to, EEG, electrocochleograph (ECOG), heart rate, ECG, blood pressure, electrical signals traversing the spinal cord or a nerve or group of nerves, and the like. The sensor or control module may analyze the biosignal(s) and may initiate electrical stimulation, or terminate electrical stimulation, in response to the biosignal(s). In at least some embodiments, the generation and delivery of electrical stimulation signals can be used in a feedback loop. For example, one or more sensors sense one or more biosignals and the electrical stimulation system generates and delivers electrical stimulation, or terminates the generation and delivery of electrical stimulation, based on the biosignal(s). If a biosignal indicates a particular abnormal or pain condition, the system may begin, or continue, to generate and deliver the electrical stimulation. The absence of the abnormal or pain condition for a predetermined period of time may cause the system to terminate the generation and delivery of electrical stimulation.

Figure 9:
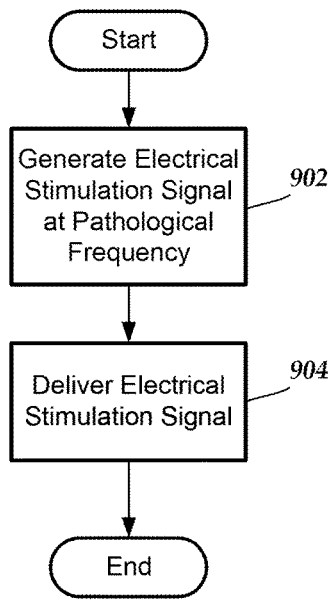
FIG. 9 is a flowchart of one embodiment of a method for generating and delivering electrical stimulation signals, according to the invention.

FIG. 9 is a flowchart of one embodiment of a method of electrical stimulation of patient tissue. In step 902, an electrical stimulation signal at a pathological frequency is generated in, for example, the control module. The electrical stimulation signal can be a series of pulses (see, for example, FIG. 5A) or a series of bursts of pulses (see, for example, FIG. 5B). In some embodiments, the electrical stimulation signal can have a continuous portion with pulses or bursts produced at the pathological frequency (see, for example, FIGS. 8A and 8B.) In step 904, the electrical stimulation system is delivered to patient tissue using one or more electrodes.

Figure 10:
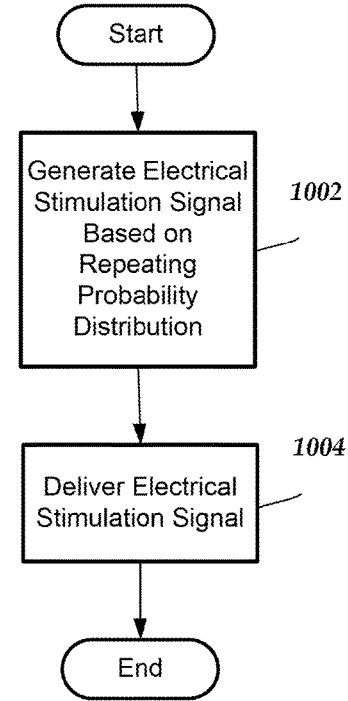
FIG. 10 is a flowchart of another embodiment of a method for generating and delivering electrical stimulation signals, according to the invention.

FIG. 10 is a flowchart of one embodiment of a method of electrical stimulation of patient tissue. In step 1002, an electrical stimulation signal is generated in, for example, the control module using a periodic repeating distribution function. The periodic repeating distribution function can be, for example, a sine wave (see, for example, FIGS. 6A and 6C), a normal distribution, a square wave, a triangular wave, a combination function (see, for example, FIG. 6B which uses a sine wave and a flat zero distribution section), or any other suitable distribution. The electrical stimulation signal can be a series of pulses (see, for example, FIGS. 6A and 6B) or a series of bursts of pulses (see, for example, FIG. 6C). In step 1004, the electrical stimulation system is delivered to patient tissue using one or more electrodes.

Figure 11:
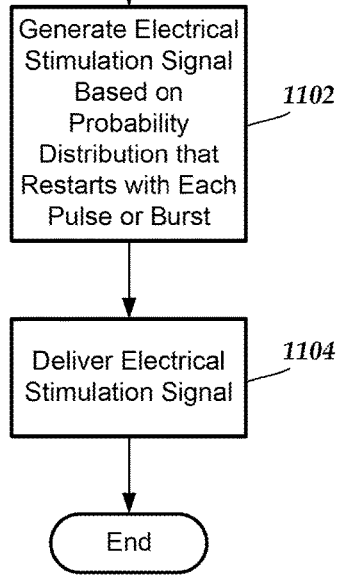
FIG. 11 is a flowchart of a further embodiment of a method for generating and delivering electrical stimulation signals, according to the invention.

FIG. 11 is a flowchart of one embodiment of a method of electrical stimulation of patient tissue. In step 1102, an electrical stimulation signal is generated in, for example, the control module using a distribution function that restarts with each pulse or burst (see, for example, FIG. 7). The periodic repeating distribution function can be, for example, a sine wave (see, for example, FIG. 7), a normal distribution, a square wave, a triangular wave, a combination function, or any other suitable distribution. The electrical stimulation signal can be a series of pulses (see, for example, FIG. 7) or a series of bursts of pulses. In step 1104, the electrical stimulation system is delivered to patient tissue using one or more electrodes.

Figure 12:
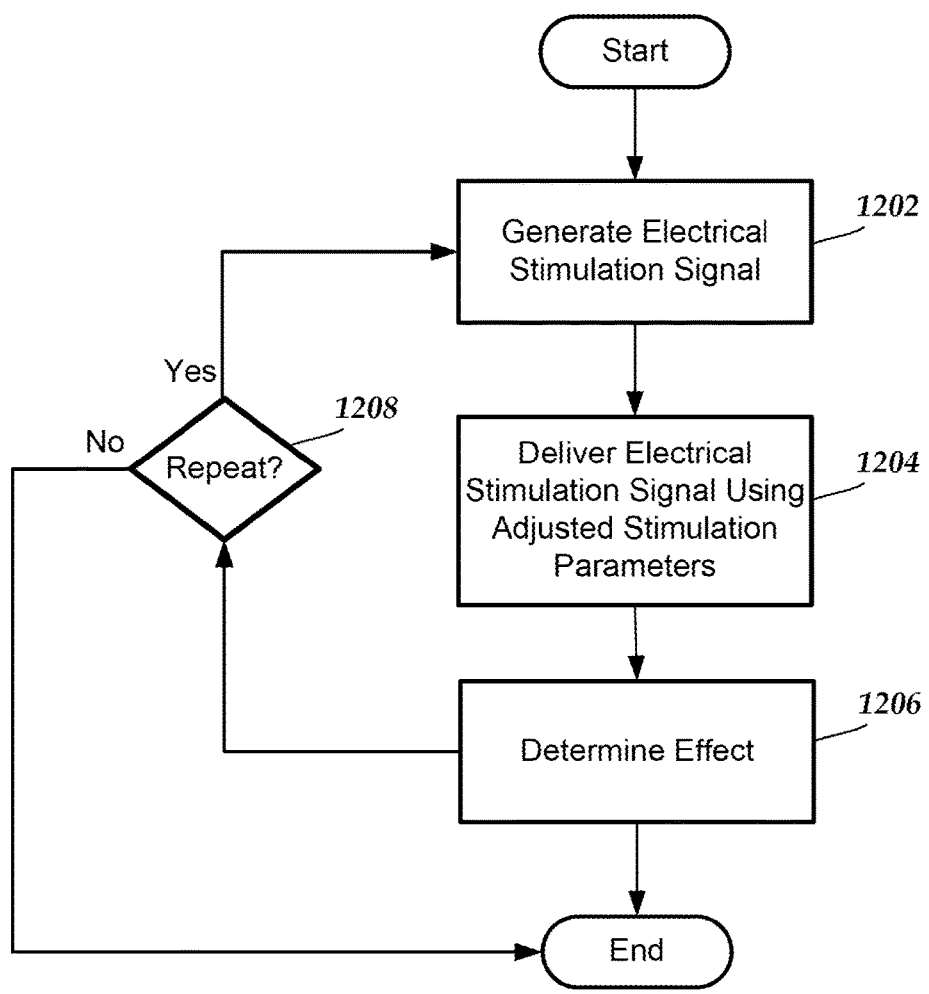
FIG. 12 is a flowchart of yet another embodiment of a method for generating and delivering electrical stimulation signals, according to the invention.

FIG. 12 is a flowchart of one embodiment of a method of electrical stimulation of patient tissue. In step 1202, an electrical stimulation signal is generated in, for example, the control module. In step 1204, the electrical stimulation system is delivered to patient tissue using one or more electrodes. These steps can be performed using any of the methods illustrated in FIGS. 9-11 or by any other suitable method.

In step 1206, the effect of the electrical stimulation signal can be determined. In at least some embodiments, the effect is determined by measuring a biosignal. Examples of suitable biosignals include, but are not limited to, EEG, electrocochleograph (ECOG), heart rate, ECG, blood pressure, electrical signals traversing the spinal cord or a nerve or group of nerves, and the like. The biosignal may be obtained from a sensor that is part of the electrical stimulation system or separate from the system. The sensor may communicate with the control module using any wired or wireless communication arrangement. In step 1208, the system or a user can decide whether to repeat the procedure to provide additional electrical stimulation or can decide to terminate the stimulation because, for example, the condition that is to be treated (for example, pain) has been reduced or alleviated as indicated by the biosignal. If the decision is to repeat, then steps 1202-1206 can be repeated as illustrate in FIG. 12.

This process can be used as a feedback loop to provide electrical stimulation to patient tissue. The feedback loop may be part of a programming session. Alternatively or additionally, the electrical stimulation system may initiate the feedback loop on a regular or irregular basis or when requested by a user, clinician, or other individual to adjust stimulation parameters.

It will be understood that the system can include one or more of the methods described hereinabove with respect to FIGS. 9-12 in any combination. The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks or described for the control modules, external programming units, systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation system, comprising:
an implantable control module configured and arranged for implantation in a body of a patient, wherein the control module is configured and arranged to provide electrical stimulation signals to an electrical stimulation lead coupled to the implantable control module for stimulation of patient tissue, wherein the implantable control module comprises
a processor configured and arranged to perform the following actions:
generating an electrical stimulation signal at a first frequency in a range of 4 to 8 Hz, wherein the electrical stimulation signal comprises a series of bursts at the first frequency, wherein each burst comprises a plurality of pulses within the burst and at a second frequency in a range from 1 kHz to 5 kHz; and delivering the electrical stimulation signal to one or more selected electrodes of an electrical stimulation lead.

2. The electrical stimulation system of claim 1, wherein the actions further comprise sensing a biosignal.

3. The electrical stimulation system of claim 2, wherein the actions further comprise repeating the generating, delivering, and sensing actions based on an analysis of the biosignal.

4. The electrical stimulation system of claim 1, further comprising a sensor in communication with the control module, wherein the actions further comprise sensing a biosignal using the sensor.

5. The electrical stimulation system of claim 1, further comprising the electrical stimulation lead coupleable to the implantable control module and comprising a plurality of electrodes disposed along a distal end portion of the electrical stimulation lead.

6. The electrical stimulation system of claim 1, wherein a temporal separation between bursts is individually selected based on a pre-determined distribution function based on the first frequency wherein the pre-determined distribution function indicates a relative likelihood that the burst will begin at a particular time.

7. The electrical stimulation system of claim 6, wherein the pre-determined distribution function is a periodic repeating distribution function.

8. The electrical stimulation system of claim 6, wherein the pre-determined distribution function is a sine distribution.

9. The electrical stimulation system of claim 6, wherein the pre-determined distribution function is a normal distribution.

10. The electrical stimulation system of claim 6, wherein the pre-determined distribution function is a distribution function that resets with each burst.

11. An electrical stimulation system, comprising:
an implantable control module configured and arranged for implantation in a body of a patient, wherein the control module is configured and arranged to provide electrical stimulation signals to an electrical stimulation lead coupled to the implantable control module for stimulation of patient tissue, wherein the implantable control module comprises
a processor configured and arranged to perform the following actions:
generating electrical stimulation pulses or pulse bursts with a temporal separation between pulses or pulse bursts is selected based on a pre-determined distribution function based on a pre-selected first frequency wherein the pre-determined distribution function indicates a relative likelihood that the pulse or pulse burst will begin at a particular time; and
delivering the electrical stimulation pulses or pulse bursts to one or more selected electrodes of an electrical stimulation lead.

12. The electrical stimulation system of claim 11, wherein the pre-determined distribution function is a periodic repeating distribution function.

13. The electrical stimulation system of claim 11, wherein the pre-determined distribution function is a sine distribution.

14. The electrical stimulation system of claim 11, wherein the pre-determined distribution function is a normal distribution.

15. The electrical stimulation system of claim 11, wherein the pre-determined distribution function is a distribution function that resets with each pulse or pulse burst.

16. The electrical stimulation system of claim 11, further comprising a sensor in communication with the control module, wherein the actions further comprise sensing a biosignal using the sensor.

17. The electrical stimulation system of claim 11, further comprising the electrical stimulation lead coupleable to the implantable control module and comprising a plurality of electrodes disposed along a distal end portion of the electrical stimulation lead.

18. An electrical stimulation system, comprising:
an implantable control module configured and arranged for implantation in a body of a patient, wherein the control module is configured and arranged to provide electrical stimulation signals to an electrical stimulation lead coupled to the implantable control module for stimulation of patient tissue, wherein the implantable control module comprises
a processor configured and arranged to perform the following actions:
generating an electrical stimulation signal, wherein the electrical stimulation signal comprises i) a continuous stimulation signal at a first frequency in a range of 4 to 8 Hz and ii) a brief burst of pulses during every period or half period of the continuous stimulation signal, wherein each brief burst of pulses comprises a plurality of pulses at a second frequency in a range from 500 Hz to 5 kHz; and
delivering the electrical stimulation signal to one or more selected electrodes of an electrical stimulation lead.

19. The electrical stimulation system of claim 18, wherein the actions further comprise sensing a biosignal.

20. The electrical stimulation system of claim 19, wherein the actions further comprise repeating the generating, delivering, and sensing actions based on an analysis of the biosignal.

* * * * *

UNITED STATES PATENT AND TRADEMARK OFFICE
CERTIFICATE OF CORRECTION

PATENT NO. : 10,004,902 B2
APPLICATION NO. : 15/799234
DATED : June 26, 2018
INVENTOR(S) : Michael A. Moffitt et al.

It is certified that error appears in the above-identified patent and that said Letters Patent is hereby corrected as shown below:

On the Title Page

Item (73) under Assignee information, please replace Lowe Graham Jones PLLC with Boston Scientific Neuromodulation Corporation Signed and Sealed this
Twenty-eighth Day of April, 2020

Andrei Iancu
*Director of the United States Patent and Trademark Office*